(12) United States Patent
Pham

(10) Patent No.: US 10,950,352 B1
(45) Date of Patent: Mar. 16, 2021

(54) SYSTEM, COMPUTER-READABLE STORAGE MEDIUM AND METHOD OF DEEP LEARNING OF TEXTURE IN SHORT TIME SERIES

(71) Applicant: Prince Mohammad Bin Fahd University, Dhahran (SA)

(72) Inventor: Tuan Duc Pham, Dhahran (SA)

(73) Assignee: Prince Mohammad Bin Fahd University, Dhahran (SA)

(*) Notice: Subject to any disclaimer, the term of this patent is extended or adjusted under 35 U.S.C. 154(b) by 0 days.

(21) Appl. No.: 16/932,281

(22) Filed: Jul. 17, 2020

(51) Int. Cl.
  *G06K 9/00* (2006.01)
  *G16H 50/30* (2018.01)
  *G16H 30/40* (2018.01)
  *G06K 9/62* (2006.01)
  *G06N 3/08* (2006.01)
  (Continued)

(52) U.S. Cl.
  CPC ............ *G16H 50/30* (2018.01); *A61B 5/1128* (2013.01); *A61B 5/4082* (2013.01); *G06F 3/011* (2013.01); *G06F 3/017* (2013.01); *G06K 9/6232* (2013.01); *G06K 9/6268* (2013.01); *G06N 3/0436* (2013.01); *G06N 3/08* (2013.01); *G16H 30/40* (2018.01); *G06T 2207/20021* (2013.01)

(58) Field of Classification Search
  CPC .......................................... G06T 2207/20021
  See application file for complete search history.

(56) References Cited

U.S. PATENT DOCUMENTS

2015/0272504 A1* 10/2015 Giancardo ........... A61B 5/1124
                                                                        600/595
2016/0241554 A1*  8/2016 Zizi .................... G06K 9/00885
(Continued)

FOREIGN PATENT DOCUMENTS

JP         2018-198028 A     12/2018

OTHER PUBLICATIONS

Pham, et al. ; Classification of Short Time Series in Early Parkinson's Disease With Deep Learning of Fuzzy Recurrence Plots ; IEEE?CAA Journal of Automatica Sinica, vol. 6, No. 6 ; Nov. 2019 ; pp. 1306-1317 ; 12 Pages.
(Continued)

*Primary Examiner* — Oneal R Mistry
(74) *Attorney, Agent, or Firm* — Oblon, McClelland, Maier & Neustadt, L.L.P.

(57) ABSTRACT

A computer-readable storage medium storing program instructions to perform a method of classification of short time series in order to detect a neurodegenerative disorder. The method includes receiving a plurality of sensor data collected from subjects with and without the neurodegenerative disorder over a period of a few seconds as the short time series, generating phase-space vectors from the plurality of sensor data in which each vector is a state of a dynamical system in space and time, transforming the phase-space vectors into a grayscale image representing recurrences of a state-space vector in the same area of the phase space, extracting temporal texture features of the grayscale image to obtain a multi-dimensional time series; inputting the multidimensional time series, without the grayscale image, to the Long Short Term Memory (LSTM) network, and classifying, by the LSTM network, the plurality of the sensor data as the neurodegenerative disorder or not.

17 Claims, 10 Drawing Sheets

(51) Int. Cl.
  *A61B 5/00*   (2006.01)
  *A61B 5/11*   (2006.01)
  *G06F 3/01*   (2006.01)
  *G06N 3/04*   (2006.01)

(56) References Cited

U.S. PATENT DOCUMENTS

| | | |
|---|---|---|
| 2016/0299938 A1 | 10/2016 | Malhotra et al. |
| 2018/0235467 A1* | 8/2018 | Celenk ................... A61B 3/14 |
| 2019/0138674 A1 | 5/2019 | Akella et al. |
| 2019/0147125 A1 | 5/2019 | Yu et al. |
| 2020/0051259 A1* | 2/2020 | Sylvestre ............. A61B 5/1455 |

OTHER PUBLICATIONS

Prasad, et al. ; Convolutional Long Short-Term Memory Hybrid Networks for Skeletal Based Human Action Recognition ; International Journal of Innovative Technology and Exploring Engineering (IJITEE) ; vol. 9, Issue 3 | Jan. 2020 ; 7 Pages.

* cited by examiner

Control FRP

PD FRP

SYSTEM, COMPUTER-READABLE STORAGE MEDIUM AND METHOD OF DEEP LEARNING OF TEXTURE IN SHORT TIME SERIES

BACKGROUND

Technical Field

The present disclosure is directed to a system, computer-readable storage medium and method for classification of short time series that uses deep learning, and in particular classification of short time series to detect and/or diagnose neurodegenerative disorders, and in particular early detection of Parkinson's disease.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

There is a need to detect neurodegenerative diseases, most notably Parkinson's disease, Huntington disease and Alzheimer's disease, at early stages so that treatments for the diseases may be most effective. Neurodegeneration is the progressive loss of structure or function of neurons, including death of neurons. Although there currently is no cure to slow disease progression, treatments such as neuromodulation may be used to treat cognitive, behavioral and psychiatric symptoms and defects.

Parkinson's disease is a progressive and degenerative brain disorder that affects an individual's muscle movement. Due to the dying of specific brain cells, people with Parkinson's disease (PD) produce less dopamine. Dopamine is a vital chemical that transmits messages to the part of the brain responsible for movement. With insufficient dopamine, a patient's movements become slower, and the symptoms of Parkinson's disease become more pronounced. Early detection and diagnosis is important because the treatments for PD are more effective in the early stages of the disease. In addition, physical therapy and exercise, which greatly improve symptoms and delay progression of the disease, are much easier to perform in the early stages.

There are generally four major stages of a disease. The first stage is referred to as incubation period followed by a prodromal period. During the prodromal period, disease symptoms may not be very specific or severe. The affected person can still perform usual functions although distress or discomfort may be felt. However, conventional therapies used for Parkinson's disease cannot slow or stop the disease in the prodromal period. See W. H. Oertel, "Recent advances in treating Parkinson's disease," *FJ000 Research*, vol. 6, pp. 260, March 2017, which is incorporated herein by reference in its entirety.

There are many techniques that use sensors for detecting and monitoring movement patterns on patients with PD. Most techniques use sensor-induced data focus on studying gait dynamics and temporal gait parameters. Other techniques use wrist accelerometers for intraoperative measurements of tremor during surgery. See J. M. Hausdorff, "Gait dynamics in Parkinson's disease: common and distinct behavior among stride length, gait variability, and fractal-like scaling," *Chaos*, vol. 19, no. 2, pp. 026113, June 2009; P. H. Chen, R. L. Wang, D. J. Liou, and J. S. Shaw, "Gait disorders in Parkinson's disease: assessment and management," *Int. J. Gerontol.*, vol. 7, no. 4, pp. 189-193, December 2013; W. Zeng, F. L. Liu, Q. H. Wang, Y. Wang, L. Ma, and Y. Zhang, "Parkinson's disease classification using gait analysis via deterministic learning," *Neurosci. Lett.*, vol. 633, pp. 268-278, October 2016; P. Ren, S. J. Tang, F. Fang, L. Z. Luo, L. Xu, M. L. Bringas-Vega, D. Z. Yao, K. M. Kendrick, and P. A. Valdes-Sosa, "Gait rhythm fluctuation analysis for neurodegenerative diseases by empirical mode decomposition," *IEEE Trans. Biomed. Eng.*, vol. 64, no. I, pp. 52-60, January 2017; T. D. Pham, "Texture classification and visualization of time series of gait dynamics in patients with neuro-degenerative diseases," *IEEE Trans. Neural. Syst. Rehabil. Eng.*, vol. 26, no. I, pp. 188-196, January 2018; S. Hemm, D. Pison, F. Alonso, A. Shah, J. Coste, J. J. Lemaire, and K. Wardell, "Patient-specific electric field simulations and acceleration measurements for objective analysis of intraoperative stimulation tests in the thalamus," *Front. Hum. Neurosci.*, vol. IO, pp. 577, November 2016, each of which are incorporated herein by reference in their entirety. One issue with using sensor data is the length of measurements. Gait measurements are obtained during relatively long walking periods, causing discomfort to the participants or are impractical for performance in clinical settings where the distance and time for walking is limited. Subsequently, research into shortening the distance and time of testing, such as determining a minimum number of strides required for a reliable estimation of temporal gait parameters, has recently been carried out with the purpose of avoiding or minimizing discomfort to participants in gait experiments. See L. Kribus-Shmiel, G. Zeilig, B. Sokolovski, and M. Plotnik, "How many strides are required for a reliable estimation of temporal gait parameters? Implementation of a new algorithm on the phase coordination index" *PLoS One*, vol. 13, no. 2, pp.e0192049, February 2018, which is incorporated herein by reference in its entirety.

As an alternative to gait and balance data, measurement of computer keystroke time series has been proposed for detecting early stages of PD. Computer keystroke time series contains information of the hold time occurring between pressing and releasing a key collected during the sessions of typing activity using a standard word processor on a personal computer. See L. Giancardo, A. Sanchez-Ferro, T. Arroyo-Gallego, I. Butterworth, C. S. Mendoza, P. Montero, M. Matarazzo, J. A. Obeso, M. L. Gray, and R. San Jose Estepar, "Computer keyboard interaction as an indicator of early Parkinson's disease," *Sci. Rep.*, vol. 6, pp. 34468, October 2016, which is incorporated herein by reference in its entirety. The data for the keystroke time series is a series of hold times (HT), which are the time between pressing and releasing a key on a laptop keyboard. In order to obtain the data, subjects typed for an average of 14 minutes with a standard word processor.

One method of detecting early stages of PD based on the computer keystroke time series data involves selection of a type of typing signal representation, then use of an ensemble approach, which is based on linear ε-Support Vector Regression, to generate neuroQWERT (nQi) scores. The nQi score is computed by generating the HT time series from a typing task that is split by non overlapping windows, then computing 7 features from the HT data set in each independent window. Four (4) of the features represent estimates of the absolute HT probability, and three (3) of the features represent different aspects of the HT variance. The output of the regression algorithm is a numerical score (one score for each of the non-overlapping HT data sets).

The typing signal representation includes only the keys for which a short hold time is expected, i.e. alphanumeric characters, symbols and space bar. In the representation, $N^w$ is the size of the window expressed in seconds. In experiments $N_w=90$. Then, a hold time signal a is partitioned with non-overlapping square windows as follows: $B_i=a[t]\omega[t-iN^w]$ where t is time, $B_i$ is a vector containing the ordered list of HT samples and i is a positive integral number which serves as an index to the list of vectors. In order to account for the sparsity of the hold time signal, i.e. typing is not performed continuously but is performed in unpredictable bursts, all $B_i$ that have less than $N^w/3$ key presses are removed from the data set. A feature vector for each $B_i$ may be defined as follows:

$$x_i = [v^{out}, v^{iqr}, v^{de}, v^{hst0}, v^{hst1}, v^{hst2}, v^{hst3}]^T$$

where $v^{out}$ is the number of outliers in $B_i$ divided by the number of elements in $B_i$. An outlier is defined as a HT more than 1.5 interquartile ranges below the first quartile or above the third quartile. $v^{iqr}$ is a measure of the $B_i$ distribution skewness described as $(q_2-q_1)/(q_3-q_1)$, and $q_n$ is the nth quartile. $v^{hstn}$ represents the nth bin of the $B_i$ equally-spaced normalized histogram, i.e. an approximation of the probability density function, with 4 bins from 0 to 0.5 seconds. $v^{de}$ is a metric of finger coordination during two consecutive keystrokes. It is measured as $d_1-p_2$, where $d_1$ is the depress event of the first key and $p_2$ is the press event of the second key. If $(d_1-p_2)<0$, then $v^{de}=0$.

The ensemble learning approach involves a combination of a set of base models F: $\{fm\ m\geq 0\hat{\ }m<N^m\}$ where $N^m$ is the total number of models, for example 200. Each model $f_m$ receives as input an independent feature vector xi and performs a linear regression step with an ε-Support Vector. fm $(x_i)$ is a linear ε-Support Vector Regression model. The result y'm is a partial estimation of the nQi score. The nQi for each xi is calculated by applying all the regression models in F on the xi vector and then calculating the median score.

In order to be successful and for practical purposes, mobile sensor data may be used as a substitute for computer keystroke time series. Finger tapping detected by the mobile sensor may be used for evaluating upper limbs motor functions. Finger tapping is typically used in clinical trials. See A. L T. Tavares, G. S. X. E. Jefferis, M. Koop, B. C. Hill, T. Hastie, G. Heit, and H. M. Bronte-Stewart, "Quantitative measurements of alternating finger tapping in Parkinson's disease correlate with UPDRS motor disability and reveal the improvement in fine motor control from medication and deep brain stimulation," *Mov. Disord.*, vol. 20, no. 10, pp. 1286-1298, October 2005, which is incorporated herein by reference in its entirety. However, the finger tapping test requires a participant to press one or two buttons on a device such as an iPhone as fast as possible for a period of time. The time duration of finger tapping needs to obtain a sufficient number of relevant features in order to distinguish a person having the disease versus not having the disease. In order to obtain the data, subjects repeatedly pressed a single button for 60 seconds, as fast as possible. In an alternative test, subjects alternately pressed two buttons for 60 seconds.

It is well known that classifying patterns using time series has many practical applications. Artificial intelligence (AI) methods for time-series classification have been implemented in many commercial products, such as sensor-based wearable devices for healthcare, self-monitoring for smart living, and unobtrusive monitoring systems using Internet of Things (IoT) and cloud technologies. Most techniques developed for time-series classification use long time series for processing partly due to a need for a sufficient number of input features. Such a requirement is not practical in many cases. For example, it is impractical to have a long corridor in a clinic along which patients with neurological disorder can walk to obtain sensor-based measurements of gait dynamics. The recording of voice for disorder detection needs to take several seconds in order to obtain a sufficient number of features.

The number of input features has an impact on accuracy in AI techniques. Too few features may lead to inability to make correct classification using a trained AI model. At the same time, too many features may not further improve accuracy of classification and will increase training time. Also, input features may impact specificity and sensitivity of classification.

The classification of time-series or sequential data, including speech recognition and machine translation, has been performed using the deep-learning method of LSTM neural networks. See Z. P. Che, S. Purushotham, K. Cho, D. Sontag, and Y. Liu, "Recurrent neural networks for multivariate time series with missing values," *Sci. Rep.*, vol. 8, no. I, pp. 6085, April 2018; G. Hinton, L. Deng, D. Yu, G. E. Dahl, A. R. Mohamed, N. Jaitly, A. Senior, V. Vanhoucke, P. Nguyen, T. N. Sainath, and B. Kingsbury, "Deep neural networks for acoustic modeling in speech recognition: the shared views of four research groups," *IEEE Signal Process. Mag.*, vol. 29, no. 6, pp. 82-97, November 2012; I. Sutskever, 0. Vinyals, and Q. V. Le, "Sequence to sequence learning with neural networks," in *Proc. 27th Int. Conj Neural Information Processing Systems*, Montreal, Canada, 2014, pp. 3104-3112; D. Bandanau, K. Cho, Y. Bengio, "Neural machine translation by jointly learning to align and translate," Eprint arXiv:1409.0473, 2014, each of which are incorporated herein by reference in their entirety. A deep recurrent neural network called TimeNet has been developed for extracting features from time series. See P. Malhotra, T. V. Vishnu, L. Vig, P. Agarwal, and G. Shroff, "TimeNet: Pre-trained deep recurrent neural network for time series classification," in *Proc. 25th European Symp. Artificial Neural Networks, Computational Intelligence and Machine Learning*, Bruges, Belgium, 2017, pp. 607-612, which is incorporated herein by reference in its entirety. The TimeNet was designed to generalize time series representations across domains. A trained TimeNet can be used as a feature extractor for time series and has been reported to be useful for time series classification by performing better than a domain-specific recurrent neural network and dynamic time warping. For example, stacked LSTM autoencoder networks were applied to extract features of time-series data, which were then used to train deep feed-forward neural networks for classification of multivariate time series recorded with sensors in the steel industry to detect steel surface defects. See N. Mehdiyev, J. Lahann, A. Emrich, D. Enke, P. Fettke, and P. Loos, "Time series classification using deep learning for process planning: a case from the process industry," *Procedia Comput. Sci.*, vol. 114, pp. 242-249, December 2017, which is incorporated herein by reference in its entirety. In this reference, the features extracted with LSTM autoencoders were found to be useful, and therefore the need for domain expert knowledge could be alleviated.

Other approaches to time-series classification that use convolutional neural networks (CNNs) have been recently introduced. In one example, a convolutional LSTM (ConvLSTM) was introduced for a spatiotemporal sequence forecasting problem in which both the input and the prediction target are spatiotemporal sequences. See X. J. Shi, Z. R. Chen, H. Wang, D. Y. Yeung, W. K. Wong, and W. C. Woo, "Convolutional LSTM network: a machine learning approach for precipitation nowcasting," in *Proc. 28th Int. Conj Neural I,iformation Processing Systems*, Montreal, Canada, 2015, pp. 802-810, which is incorporated herein by reference in its entirety. The ConvLSTM model was constructed by extending the fully connected LSTM to have convolutional structures in the input-to-state and state-to-state transitions. The ConvLSTM model was reported to perform better than the fully connected LSTM in that it is able to capture the spatiotemporal correlations of the sequential data for precipitation nowcasting. In another example, a multi-scale convolutional neural network, which extracts deep-learning features at different scales and frequencies from three representations of time series, including the original, down-sampled, and smoothed data, was reported to be capable of extracting effective features for time series classification. Baseline full convolutional networks were proposed for time series classification. See Z. C. Cui, W. L. Chen, and Y. X. Chen, "Multi-scale convolutional neural networks for time series classification," Eprint arXiv: 1409.0473, 2016; Z. G. Wang, W. Z. Yan, and T. Oates, "Time series classification from scratch with deep neural networks: a strong baseline," in *Proc. 2017 Int. Joint Conj Neural Networks*, Anchorage, USA, 2017, pp. 1578-1585, each of which are incorporated herein by reference in their entirety. The proposed baseline models were reported to be pure end-to-end without demanding heavy pre-processing of the raw data or feature crafting, and achieve performance that is comparative to other state-of-the-art approaches, including the multilayer perceptron, full convolutional network, and residual network. These models consist of a branching structure. The first branch is the convolutional part, whereas the second branch is an LSTM block which receives a time series in a transposed form as multivariate time series with a single time step. The outputs of the two branches are concatenated and then fed to a classifier. These models were reported to be able to enhance the performance of a full convolutional networks with a nominal increase in model size as well as require minimal data pre-processing.

In general, time-series classification has been recognized as an important and challenging area of research, particularly with respect to the increasing availability of new data for time series. While numerous algorithms for time-series classification have been published in literature and the popularity of deep learning has been pervasive in many disciplines, only a few deep neural networks have been applied to solving time-series classification problems.

It is one object of the present disclosure to describe a system and method that can perform classification with a very short time series. It is a further object to improve classification accuracy by incorporating fuzzy recurrence plots of the short time series into LSTM models.

SUMMARY

An aspect of the present disclosure is a method of classification of short time series in order to detect a neurodegenerative disorder. The method includes receiving, by circuitry, a plurality of sensor data collected from subjects with and without the neurodegenerative disorder over a period of a few seconds as the short time series; generating, by the circuitry, phase-space vectors from the plurality of sensor data in which each vector is a state of a dynamical system in space and time; transforming, by the circuitry, the phase-space vectors into a grayscale image representing recurrences of a state-space vector in the same area of the phase space, wherein the intensity distribution of the grayscale image takes values in the range of 0 to 1; for every pixel of the grayscale image, selecting, by the circuitry, a local window, where the respective pixel is at a center of the local window; extracting, by the circuitry, temporal texture features of each window to obtain a multi-dimensional time series of D texture dimensions; inputting, by the circuitry, the multidimensional time series, without the grayscale image, to the Long Short Term Memory (LSTM) network; and classifying, by the LSTM network, the plurality of the sensor data as the neurodegenerative disorder or not.

Another aspect of the present disclosure is a non-transitory computer-readable storage medium storing computer program instructions. When executed by a computer the computer program instructions perform a method of classification of short time series in order to detect a neurodegenerative disorder, including receiving a plurality of sensor data collected from subjects with and without the neurodegenerative disorder over a period of a few seconds as the short time series; generating phase-space vectors from the plurality of sensor data in which each vector is a state of a dynamical system in space and time; transforming the phase-space vectors into a grayscale image representing recurrences of a state-space vector in the same area of the phase space, wherein the intensity distribution of the grayscale image takes values in the range of 0 to 1; for every pixel of the grayscale image, selecting a local window, where the respective pixel is at a center of the local window; extracting temporal texture features of each window to obtain a multi-dimensional time series of D texture dimensions; inputting the multidimensional time series, without the grayscale image, to the Long Short Term Memory (LSTM) network; and classifying, by the LSTM network, the plurality of the sensor data as the neurodegenerative disorder or not.

Another aspect of the present disclosure is a method of classification of short time series in order to detect a neurodegenerative disorder. The method includes receiving, by circuitry, a plurality of sensor data collected from subjects with and without the neurodegenerative disorder over a period of a few seconds as the short time series; generating, by the circuitry, phase-space vectors from the plurality of sensor data in which each vector is a state of a dynamical system in space and time; transforming, by the circuitry, the phase-space vectors into a grayscale image representing recurrences of a state-space vector in the same area of the phase space, wherein the intensity distribution of the grayscale image takes values in the range of 0 to 1; inputting, by the circuitry, the grayscale image representation to a Long Short Term Memory (LSTM) network; and classifying, by the LSTM network, the plurality of the sensor data as the neurodegenerative disorder or not.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
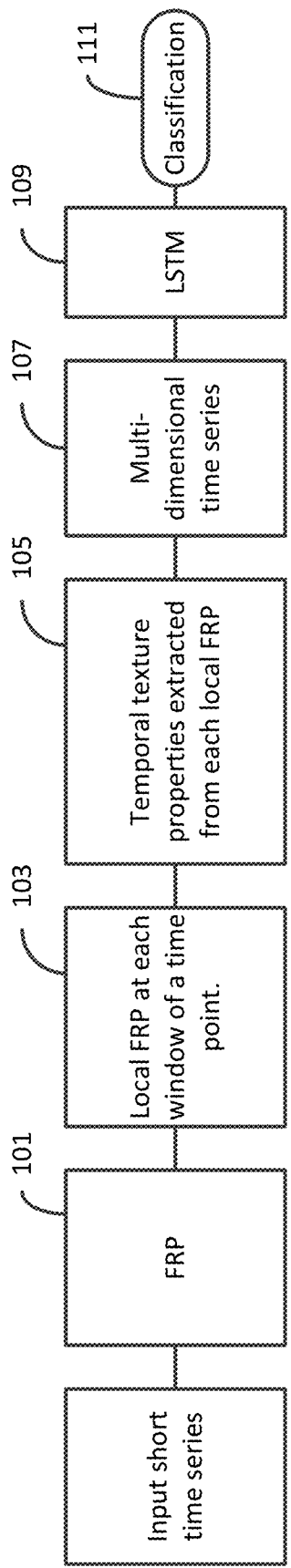
FIG. 1 is a block diagram of an architecture of a Long Short Term Memory network for time-series classification in accordance with an exemplary aspect of the disclosure.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise or illustrating schematic structures or flowcharts.

Aspects of this disclosure are directed to a technique that uses very short time series for machine classification, and particularly a method in which temporal texture features of each window are extracted to obtain multi-dimensional time series. The extraction of temporal texture features may be performed by determining a gray-level co-occurrence matrix, extracting local binary patterns, or determining spatial statistics of each window. The technique includes extracting temporal texture features from each local window, where the local window is selected for pixels of a fuzzy recurrence plot. By using texture features instead of grayscale values of the fuzzy recurrent plot (FRP), the disclosure achieves 1) greater classification performance by incorporating more effective features, 2) more robustness in handling various types of short time series by being able to take into account local spatio-temporal properties of complex data, and 3) significant reduction in training time and memory required by deep neural networks as the number of texture features can be much smaller than the size of the FRPs. The technique can be embedded into low-cost mobile communication devices such as iPhones, smartphones, and iPads for automated detection of pathological conditions, such as human voice disorders (dysphonia), stress, emotion, and gait dynamics in patients with neurological disorders, including Parkinson's disease, Huntington disease and Alzheimer's disease.

FIG. 1 is a block diagram of an architecture of a Long Short Term Memory network for time-series classification in accordance with an exemplary aspect of the disclosure. The architecture may perform a pipeline process that classifies data for short time series. The pipeline process is a chain of sub-processes in which the output of one sub-process is an input to a next sub-process. Some buffering may be performed between each consecutive sub-process. In 101, a short time series is transformed into a fuzzy recurrence plot (FRP), which has been defined as a grayscale texture image reflecting the underlying dynamics of the time series. See T. D. Pham, Fuzzy recurrence plots, EPL (Europhysics Letters), 116 (2016) 50008; J. P. Eckmann, S. O. Kamphorst, D. Ruelle, Recurrence plots of dynamical systems, Europhysics Letters, 5 (1987) 973-977, each of which are incorporated herein by reference in their entirety. In 103, for every pixel of the FRP, a local window, where the pixel is at the center, is selected. A window that requires values from beyond the image boundaries will take those of mirrored pixels. Mirrored pixels are pixels located on the opposite side of the window center. In 105, temporal texture features, such as the gray-level co-occurrence matrix (GLCM), local binary patterns (LBP), spatial statistics, and other texture properties, of each window are extracted (see Table 1). See R. M. Haralick, K. Shanmugam, I. Dinstein, Textural features for image classification, IEEE Transactions on Systems, Man, and Cybernetics, 3 (1973) 610-621; T. Ojala, M. Pietikainen, T. Maenpaa, Multiresolution gray scale and rotation invariant texture classification with local binary patterns, IEEE Transactions on Pattern Analysis and Machine Intelligence, 24 (2002) 971-987; T. D. Pham, The semi-variogram and spectral distortion measures for image texture retrieval, IEEE Transactions on Image Processing, 25 (2016) 1556-1565, each of which are herein incorporated by reference in their entirety. The GLCM represents how often a pixel with a gray-level value i occurs either horizontally, vertically, or diagonally to adjacent pixels with a gray-level value j. The GLCM can be used to derive several statistics that characterize the texture of the image, including contrast, correlation, energy, and homogeneity. The LBP is a feature vector determined over a window of pixels and may be used to define texture of the image. Geostatistics are other measures of texture that are particularly useful for characterizing landcover.

Each temporal texture feature (statistical information) may be considered as a dimension of the time series, thus expanding the time series into a multi-dimensional time series of D texture dimensions 107. The multi-dimensional time series can be used as an input into the long short-term memory (LSTM) network 109. The LSTM network 109 is an artificial recurrent neural network for deep learning that, as mentioned above, can be used for classification of short time series. The output of the LSTM network 109 is a classification 111. Thus, the time series are transformed from one-dimensional data into multi-dimensional data with features being already widely proved effective for pattern classification. The expansion of the number of features enables sufficient performance of deep learning of the LSTM network 109.

TABLE 1

Texture features of a fuzzy recurrence plot extracted from several methods

| Texture Analysis methods | Features |
| --- | --- |
| Gray-level co-occurrence matrix (GLCM) | Entropy, energy, correlation, contrast, sum average, sum variance, sum entropy, difference variance, difference entropy, information measures of correlation, autocorrelation, dissimilarity, homogeneity, cluster prominence, cluster shade, maximum probability, inverse difference |
| Local binary patterns (LBP) | Local texture information |
| Geostatistics | Spatial statistical information |
| Others | Others |

Further regarding the fuzzy recurrence plot (FRP), the development of constructing a FRP of a time series was inspired with the concept of a recurrence plot (RP). An RP is a visualization method for studying patterns of chaos in time series. See J. P. Eckmann, S. 0. Kamphorst, and D. Ruelle, "Recurrence plots of dynamical systems," *EPL*

(*Europhys. Lett.*) vol. 4, no. 9, pp. 973-977, November 1987, which is incorporated herein by reference in its entirety. An RP shows the times at which a phase-space trajectory approximately revisits the same area in the phase space.

Based on the Takens' embedding theorem in the study of dynamical systems, a phase-space reconstruction of a time series can be obtained using an embedding dimension m and time delay τ. See F. Takens, "Detecting strange attractors in turbulence," in *Dynamical Systems and Turbulence, Warwick 1980: Proceedings of a Symposium Held at the University of Warwick* 1979/80, D. Rand, and L. S. Young, Eds. Berlin, Heidelberg: Springer, 1981, pp. 366-381, which is incorporated herein by reference in its entirety. In particular, let $X=(x_1, \ldots, x_N)$ be a collection of phase-space vectors, in which $x_i$ is the i-th state of a dynamical system in m-dimensional space and time delay. An FRP represents the recurrences of xi, which visits the same area in the phase space, as a grayscale image whose intensity distribution takes values in [0, 1].

In formulating the FRP, let V={v} be the set of fuzzy clusters of the phase-space vectors. A binary relation, relation R from X to V, is a fuzzy subset of X×V characterized by a fuzzy membership function μ in [0, 1]. This fuzzy membership grade is the degree of relation of each pair (xi, vj) in R̃, i=1, ..., N, j=1, ..., c, that has the following properties:

Reflexivity: $\mu(x_i, x_i)=1$, $\forall x \in X$,
Symmetry: $\mu(x_i, v_j)=\mu(v_j, x_i)$, $\forall x \in X$, $\forall v \in V$, and
Transitivity: $\mu(x_i, x_k)=\vee_v[\mu(x_i, v_j) \wedge \mu(v_j, x_k)]$, $\forall x \in X$, which is called the max-min composition, where the symbols $\vee$ and $\wedge$ stand for max and min, respectively.

Reflexivity is a property that every element in a set X has a relation to itself. Symmetry is a property if any element x has a relation to an element v, then v has the same relation to x. Transitivity is a property that if any element $x_i$ has a relation to an element v, ant the element v has the same relation to another element $x_k$, then $x_i$ has the relation to $x_k$. Fuzzy membership grades for elements are similar if they meet these three properties (Reflexivity, Symmetry, Transitivity).

If the fuzzy membership function that indicates the similarity between the phase space trajectory at two different times (visiting the same area in the phase space) can be obtained, the above three properties of an FRP can be readily constructed. A solution for computing the fuzzy membership function (clustering similar elements) can be determined by using the fuzzy c-means algorithm. The fuzzy c-means algorithm attempts to partition a collection of elements into a collection of c fuzzy clusters.

By specifying several clusters c for the data, the fuzzy c—means algorithm is applied to identify the fuzzy clusters of the phase-space vectors and determine the similarity between the phase states and the fuzzy cluster centers. See J. C. Bezdek, *Pattern Recognition with Fuzzy Objective Function Algorithms*. New York: Plenum Press, 1981, which is incorporated herein by reference in its entirety. Based on this direct similarity measure, the inference of the similarity between the pairs of the phase states can be carried out using the max-min composition of a fuzzy relation.

In particular, the fuzzy membership of $x_i$ assigned to a cluster center $v_j$ of X, $\mu(x_i, v_j)$ or denoted as is computed using the fuzzy c-means (FCM) algorithm that attempts to partition N elements of X into a set of c fuzzy clusters, 1<c<N, by minimizing the following objective function F:

$$F = \sum_{i=1}^{N} \sum_{k=1}^{c} (\mu_{ij})^w \|x_i - v_j\|^2 \qquad (3)$$

where $w \in (1, \infty)$ is the fuzzy weighting exponent, and F is subject to $$\sum_{j=1}^{c} \mu_{ij} = 1, i = 1, \ldots, N. \qquad (4)$$

The minimization of the objective function of the FCM is numerically carried out by an iterative process of updating the fuzzy membership grades and cluster centers until the convergence or maximum number of iterations is reached. The fuzzy membership grades and cluster centers are updated as $$\mu_{ij} = \frac{1}{\sum_{q=1}^{c} \left(\frac{\|x_i - v_j\|}{\|x_i - v_q\|}\right)^{2/(w-1)}}, \qquad (5)$$

$$v_j = \frac{\sum_{i=1}^{N} (\mu_{ij})^w x_i}{\sum_{i=1}^{N} (\mu_{ij})^w}, j = 1, \ldots, c. \qquad (6)$$

Using the values of the fuzzy membership derived from the FCM and the fuzzy relation to represent the degree of recurrence among the phase-space vectors of the time series, an FRP can be visualized as a grayscale image by taking the complement of the FRP matrix that displays a black pixel if $x_i=x_k$, i, j=1, ..., N, otherwise a pixel is assigned a shade of gray.

The disclosed LSTM network learning for deep learning of texture in a short time series can be further explained as follows. An LSTM neural network is an artificial recurrent neural network (RNN) used in deep learning. See S. Hochreiter and J. Schmidhuber, "Long short-term memory," *Neural Comput.*, vol. 9, no. 8, pp. 1735-1780, November 1997, which is incorporated herein by reference in its entirety. Unlike conventional feedforward neural networks, an LSTM model has feedback loops that allow information of previous events to be carried on in the sequential learning process. Therefore, LSTM networks are effective in learning and classifying sequential data such as speech and video analysis. See A. Graves and J. Schmidhuber, "Framewise phoneme classification with bidirectional LSTM and other neural network architectures," *Neural Netw., vol.* 18, no. 5-6, pp. 602-610, July-August 2005; A. Graves, N. Jaitly, and A. R. Mohamed, "Hybrid speech recognition with Deep Bidirectional LSTM," in *Proc.* 2013 *IEEE Workshop on Automatic Speech Recognition and Understanding*, Olomouc, Czech Republic, 2013, pp. 273-278; R. Zazo, A. Lozano-Diez, J. Gonzalez-Dominguez, D. T. Toledano, and J. Gonzalez-Rodriguez, "Language identification in short utterances using long short-term memory (LSTM) recurrent neural networks," *PLoS One*, vol. 11, no. 1, pp.e0146917, January 2016; Z. Y. Li, K. Gavrilyuk, E. Gavves, M. Jain, and C. G. M. Snoek, "VideoLSTM convolves, attends and flows for action recognition," *Comput. Vision Image*

*Underst.*, vol. 166, pp. 4 1-50, January 2018, each of which are incorporated herein by reference in their entirety.

Figure 2A:
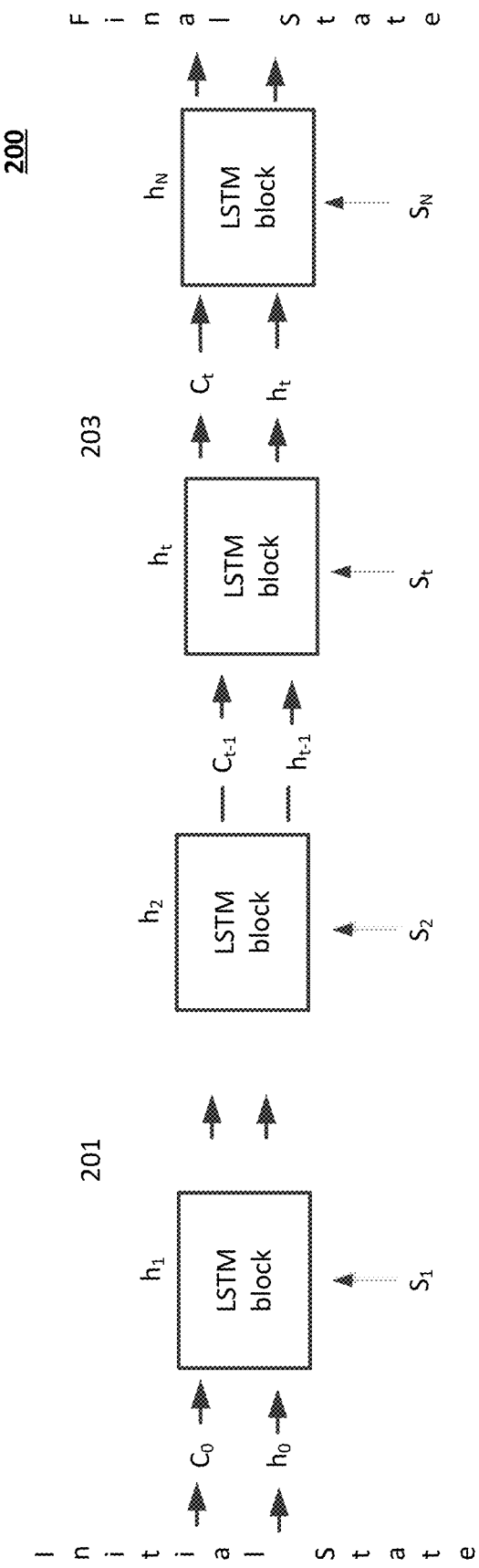
FIGS. 2A and 2B are diagrams of a layer and a cell of the Long Short Term Memory network.
Figure 2B:
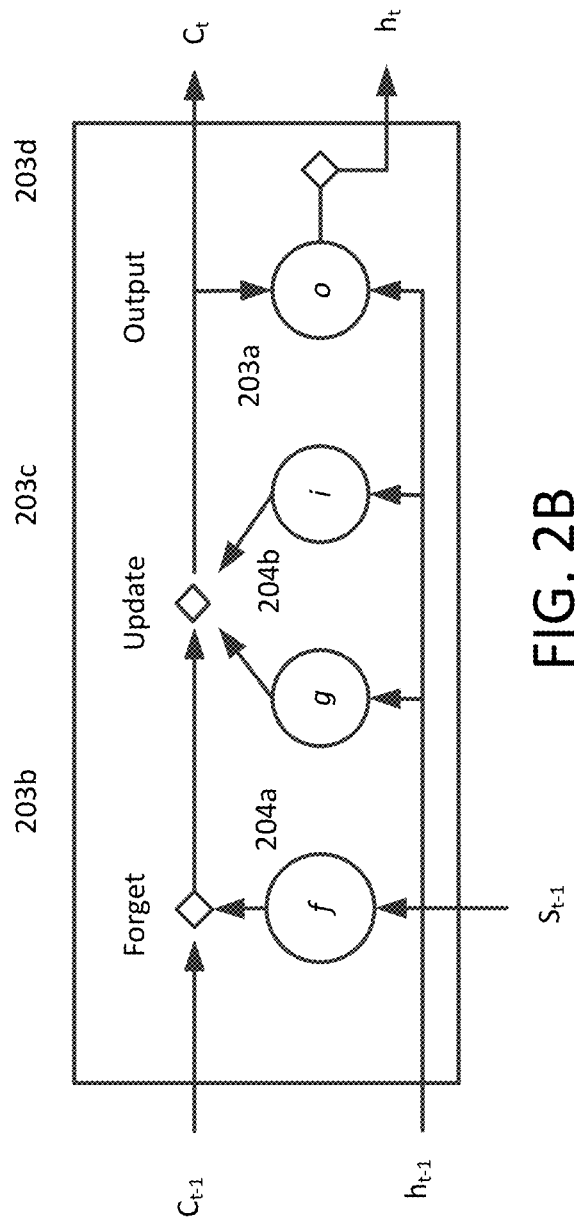

FIGS. 2A and 2B are diagrams of a layer and a cell of the Long Short Term Memory network. The LSTM network performs deep learning of texture-based time series, where each dimension of time series is represented with a texture feature. For an LSTM layer, the first LSTM block 201 takes the initial state of the network $c_0$ and the first time step of time series of multiple texture features $h_0$, and then computes the first output $h_1$ and the updated cell state $c_1$, then at time step t, the LSTM block 203 takes the current state of the network $c_{t-1}$, $h_{t-1}$ and the next time step of the FRP at t, and then computes the output $h_t$ and the updated cell state $c_t$.

The internal state of an RNN is used as a memory cell to map real values of input sequences to those of output sequences that reflect the dynamic pattern of time series, and therefore is considered an effective algorithm for learning and modeling temporal data. See T. Mikolov, S. Kombrink, L. Burget, J. H. Cemocky, and S. Khudanpur, "Extensions of recurrent neural network language model," in *Proc. 2011 IEEE Int. Conj Acoustics, Speech and Signal Processing*, Prague, Czech Republic, 2011, pp. 5528-5531, which is incorporated herein by reference in its entirety. However, because an RNN uses sequential processing over time steps that can easily degrade the parameters capturing short-term dependencies of information sequentially passing through all cells before arriving at the current processing cell. This effect causes the gradient of the output error with respect to previous inputs to vanish by the multiplication of many small numbers being less than zero. This problem is known as vanishing gradients. See R Pascanu, T. Mikolov, and Y. Bengio, "On the difficulty of training recurrent neural networks," in *Proc. 30th i nt. Conj Machine Learning*, Atlanta, Ga., USA, 2013, pp. III-1310-III-1318, which is incorporated herein by reference in its entirety. LSTM networks attempt to overcome the problem of the vanishing gradients encountered by conventional RNNs by using gates to keep relevant information and forget irrelevant information.

The difference between an LSTM neural network and a conventional RNN is the use of memory blocks for the former network instead of hidden units for the latter. See K. Greff, R. K. Srivastava, J. Koutnik, B. R. Steunebrink, and J. Schmidhuber, "LSTM: a search space odyssey," *JEEE Trans. Neural Netw. Learn. Syst.*, vol. 28, no. IO, pp. 2222-2232, October 2017, which is incorporated herein by reference in its entirety. The input gate of an LSTM network guides the input activations into the memory cell and the output gate carries out the output flow of cell activations into the rest of the network. The forget gate 203b allows the flow of information from the memory block to the cell as an additive input, therefore adaptively forgetting or resetting the cell memory. Thus, being less sensitive to the time steps makes LSTM networks better for analysis of sequential data than conventional RNNs. A common LSTM model is composed of a memory cell, an input gate 203a, an output gate 203d, and a forget gate 203b. The cell memorizes values over time steps and the three gates control the flow of information into and out of the cell. The weights and biases to the input gate regulate the amount of new value flowing into the cell, while the weights and biases to the forget gate 203b and output gate 203d control the amount of information to remain in the cell and the extent to which the value in the cell is used to compute the output activation of the LSTM block, respectively.

The architecture for LSTM receives the fuzzy membership grades of the FRP 101 as the input values, as shown in FIG. 1. Furthermore, it can be visualized from FIG. 1 that the use of FRPs can increase the feature of a time series from one dimension to N dimensions, where N is the number of the phase-space vectors of the time series, enhancing the training of the LSTM network. FIG. 2B shows the forget 203b, update 203c, and output 203d gates of the cell and hidden states. The mathematical expressions for the four gates of an LSTM block at time step t with the input of a FRP 101 represented with its discrete fuzzy membership vector of N dimensions at time t, denoted as $\mu_t = (\mu_t^1, \mu_t^2, \ldots \mu_t^N)^T$, are given as follows. See S. Hochreiter and J. Schmidhuber, "Long short-term memory," *Neural Comput*, vol. 9, no. 8, pp. 1735-1780, November 1997, which is incorporated herein by reference in its entirety.

$$f_t = \sigma_g(W_f \mu_t + R_f h_{t-1} + b_f) \tag{7}$$

where $f_t \in \mathbb{R}^N$ is the activation vector of the forget gate at time t, $\sigma_g$ denotes the sigmoid function, $W_f \in \mathbb{R}^{M \times N}$ is the input weight matrix, M refers to the number of hidden layers, $R_f \in \mathbb{R}^{M \times M}$ is the recurrent weight matrix, $h_{t-1} \in \mathbb{R}^M$ is the hidden state vector at time (t−1), which is also known as the output vector of the LSTM unit and the initial $h_0=0$, and $b_f \in \mathbb{R}^M$ is the bias vector of the forget gate 203b.

The input gate 203a at time t, denoted as $i_t \in \mathbb{R}^M$, is expressed as $$i_t = \sigma_g(W_i \mu_t + R_i h_{t-1} + b_i) \tag{8}$$

where $W_i$, $R_i$, and $b_i$, are similarly defined as in (7).

The cell candidate vector that adds information to the cell state at time step t, denoted as $g_t \in \mathbb{R}^M$ 204b, is defined as $$g_t = \sigma_c(W_g \mu_t + R_g h_{t-1} + b_g) \tag{9}$$

where $\sigma_c$ is hyperbolic tangent function (tanh), $W_g$, $R_g$, and $b_g$ are similarly defined as in (7).

The output gate 203d, denoted as $o_t \in \mathbb{R}^M$, which controls the level of the cell state added to hidden state is expressed as $$o_t = \sigma_g(W_o \mu_t + R_o h_{t-1} + b_o) \tag{10}$$

where $W_o$, $R_o$, and $b_o$ are similarly defined as in (7).

The cell state vector at time step t, denoted as $c_t \in \mathbb{R}^M$, is given by $$c_t = f_t \circ c_{t-1} + i_t \circ g_t \tag{11}$$

where the initial values for $c_0=0$, and the operator $\circ$ denotes the Hadamard product.

Finally, the hidden state vector at time step t is given by $$h_t = o_t \circ \sigma_c(c_t). \tag{12}$$

Regarding FIG. 1, the LSTM network starts with an input layer of time series followed by an LSTM layer. To predict class labels, the LSTM network may end with a fully connected layer, a softmax layer, and a classification output layer.

Texture features extracted from an FRP are the input values that play the role in creating multiple dimensions for the time series to enhance the LSTM-network training. The original time points of the time series are now replaced with reduced time points on the FRP.

Figure 3:
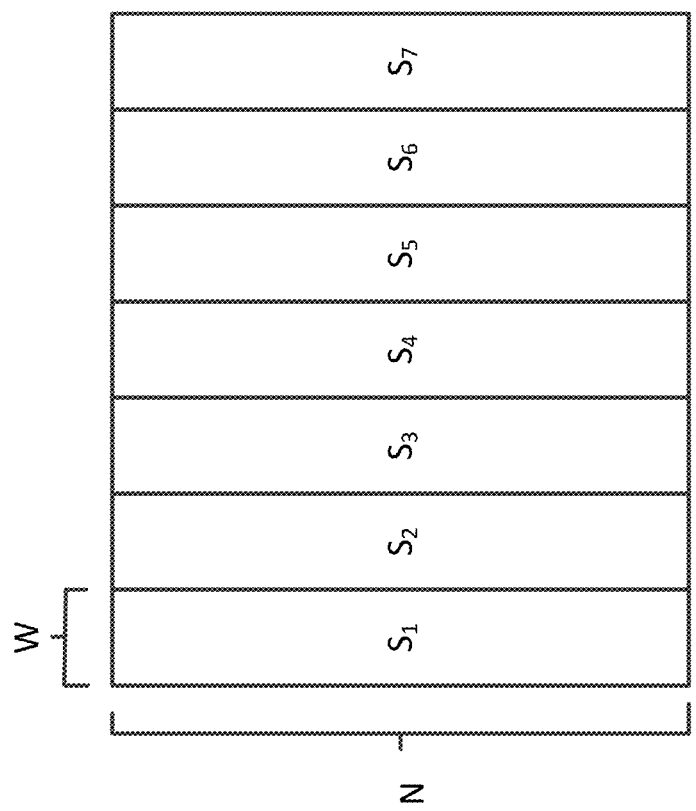
FIG. 3 illustrates the construction of the subimages of an FRP or local FRPs for texture extraction.

Thus, instead of learning from the direct input of time series, the LSTM is fed with temporal texture features as multiple dimensions at the time points on the FRP. The extraction of temporal texture features from an FRP for the LSTM learning may be carried out by dividing the FRP into subimages S having a width w<N pixels. FIG. 3 illustrates the construction of the subimages of an FRP or local FRPs for texture extraction. The process is done on either the top row, which is FRP(1,:), or far left column, which is FRP(:,1), of the FRP. Consider that the width w is taken along the top row of the FRP. Subimages of size N-by-w are therefore created out of the FRP for the timewise extraction of texture features. The N-by-w subimages are constructed by starting at the first column of the FRP and sequentially dividing it into smaller images with a non-overlapping interval of w pixels until the last column of the FRP is included. The width of the last subimage can be smaller than w if the ratio of N to w is a non-integer.

The present disclosure shows that the incorporation of FRPs of short time series, which creates multiple dimensions or channels for each time step of the time series, as input into the LSTM model can improve the LSTM-based classification and outperform the direct classification of time series using a 1DCNN model as the baseline. In an exemplary implementation, the number of dimensions associated with the time steps of a sequence is used as the number of features transferred through an LSTM layer, which constitutes a LSTM layer architecture as described by LSTM networks in the MATLAB deep learning toolbox (R2018b and R2019a). The core components of an LSTM network are a time-series input layer and an LSTM layer. The input layer inputs time series data into the network. An LSTM layer learns long-term dependencies between time steps of the data.

Furthermore, by using texture features instead of grayscale values of the FRPs, disclosed embodiments achieve 1) improved classification performance by incorporating more effective features, 2) more robustness in handling various types of short time series by being able to take into account local spatio-temporal properties of complex data, and 3) significant reduction in training time and memory required by deep neural networks as the number of texture features can be much smaller than the size of the FRPs.

The present disclosure may be implemented in low-cost mobile communication devices such as iPhones, smartphones, and iPads for automated detection of pathological conditions, such as human voice disorders (dysphonia), stress, emotion, and gait dynamics in patients with neurological disorders. Implementations may also include a Computer Voice Stress Analyzer, voice analysis technology for emotion detection, personality and risk assessment, systems for gait phase detection, and machine learning techniques for detecting voice disorder in patients with muscle tension dysphonia.

[Mobile Device]

In one implementation, the functions and processes of the mobile device 450 may be implemented by one or more respective processing circuits 426. A processing circuit includes a programmed processor as a processor includes circuitry. A processing circuit may also include devices such as an application specific integrated circuit (ASIC) and conventional circuit components arranged to perform the recited functions. Note that circuitry refers to a circuit or system of circuits.

Figure 4:
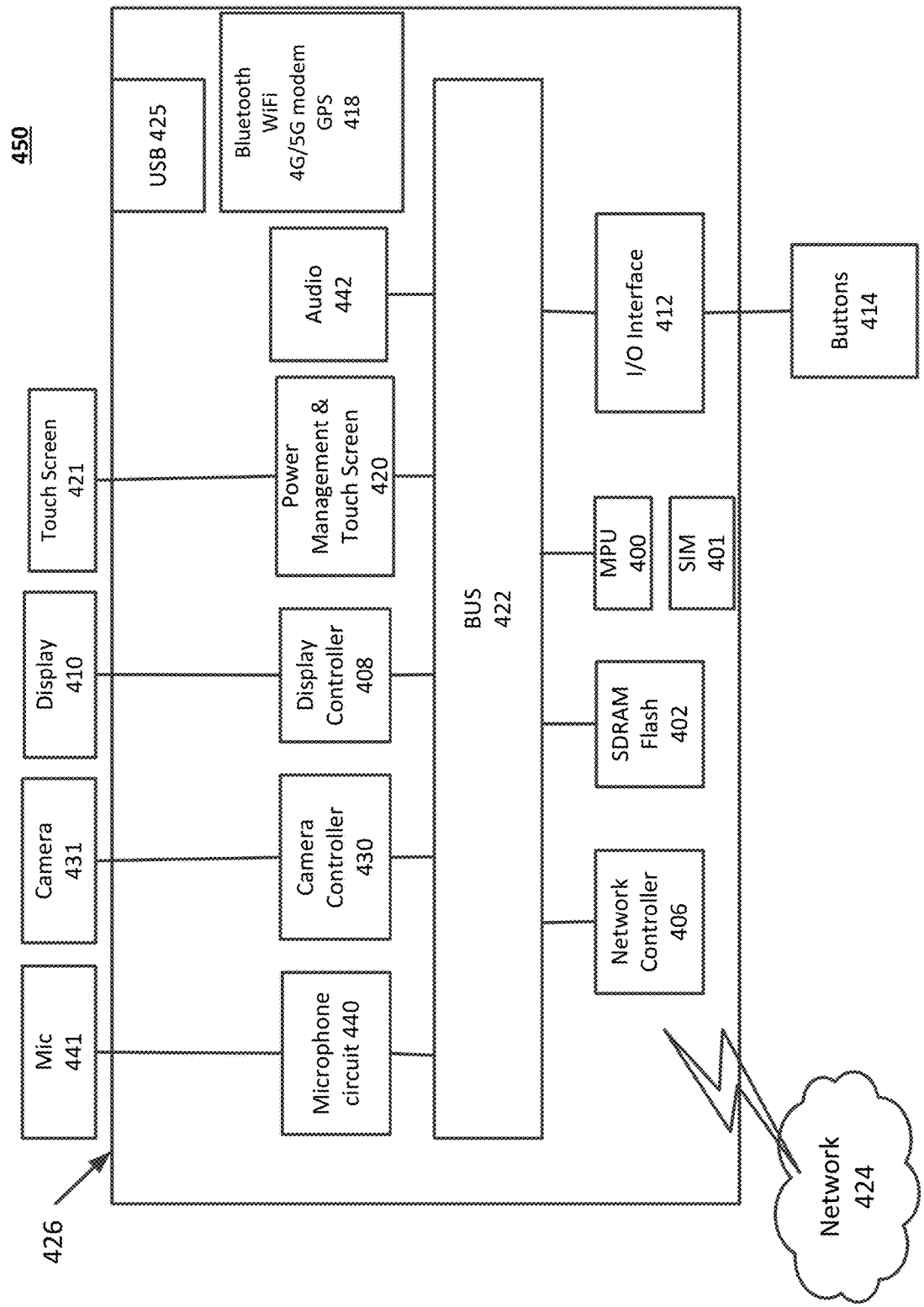
FIG. 4 is a block diagram of a computer system for implementing the Long Short Term Memory network for time-series classification.
Figure 5A:
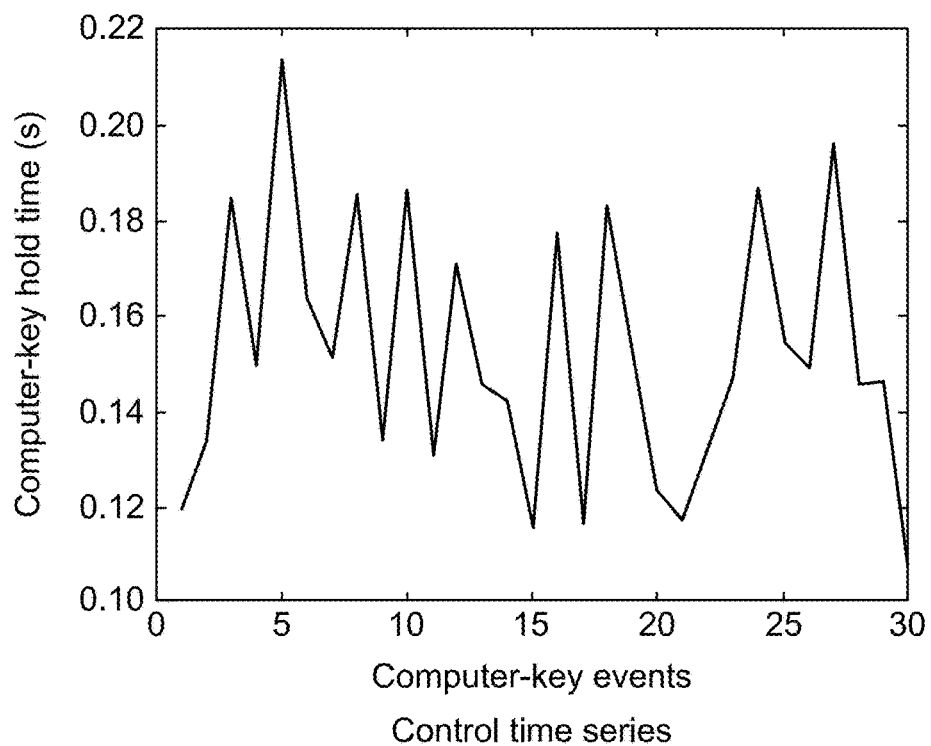
FIGS. 5A, 5B, 5C, 5D are graphs of time series and corresponding FRPs of a control subject and early PD subject.
Figure 5B:
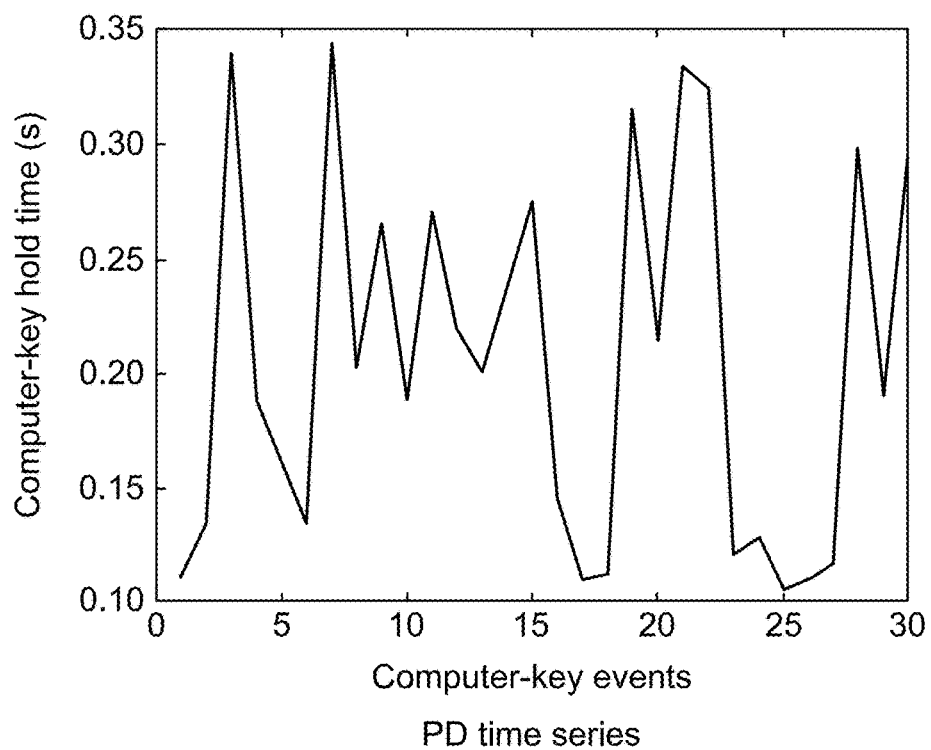
Figure 5C:
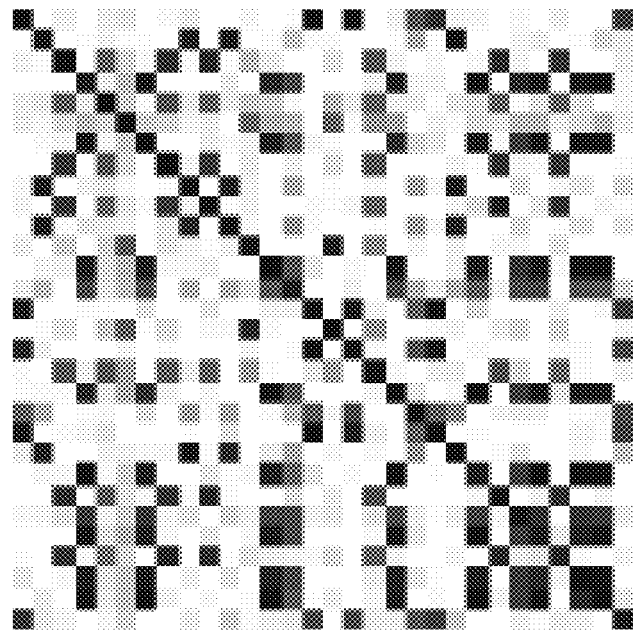
Figure 5D:
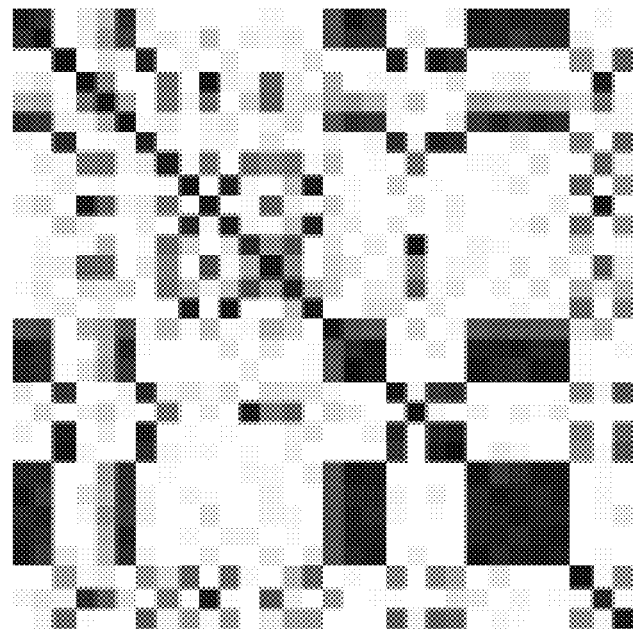

Next, a hardware description of the processing circuit 426 according to exemplary embodiments is described with reference to FIG. 4. In FIG. 4, the processing circuit 426 includes a Mobile Processing Unit (MPU) 400 which performs the processes described herein. The process data and instructions may be stored in memory 402. These processes and instructions may also be stored on a portable storage medium or may be stored remotely. The processing circuit 426 may have a replaceable Subscriber Identity Module (SIM) 401 that contains information that is unique to the network service of the mobile device 450.

Further, the claimed advancements are not limited by the form of the computer-readable media on which the instructions of the inventive process are stored. For example, the instructions may be stored in FLASH memory, Secure Digital Random Access Memory (SDRAM), Random Access Memory (RAM), Read Only Memory (ROM), Programmable Read-Only Memory (PROM), Erasable Programmable Read-Only Memory (EPROM), Electrically Erasable Programmable Read Only Memory (EEPROM), solid-state hard disk or any other information processing device with which the processing circuit 426 communicates, such as a server or computer.

Further, example implementations may be provided as a utility application, background daemon, or component of an operating system, or combination thereof, executing in conjunction with MPU 400 and a mobile operating system such as Android, Microsoft® Windows® 10 Mobile, Apple iOS® and other systems known to those skilled in the art.

In order to achieve the processing circuit 426, the hardware elements may be realized by various circuitry elements, known to those skilled in the art. For example, MPU 400 may be a Qualcomm mobile processor, a Nvidia mobile processor, a Atom® processor from Intel Corporation of America, a Samsung mobile processor, or a Apple A7 mobile processor, or may be other processor types that would be recognized by one of ordinary skill in the art. Alternatively, the MPU 400 may be implemented on an Field-Programmable Gate Array (FPGA), Application Specific Integrated Circuit (ASIC), Programmable Logic Device (PLD) or using discrete logic circuits, as one of ordinary skill in the art would recognize. Further, MPU 400 may be implemented as multiple processors cooperatively working in parallel to perform the instructions of the inventive processes described above.

The processing circuit 426 in FIG. 4 also includes a network controller 406, such as an Intel Ethernet PRO network interface card from Intel Corporation of America, for interfacing with network 424. As can be appreciated, the network 424 can be a public network, such as the Internet, or a private network such as LAN or WAN network, or any combination thereof and can also include PSTN or ISDN sub-networks. The network 424 can also be wired, such as an Ethernet network. The processing circuit may include various types of communications processors for wireless communications including 3G, 4G and 5G wireless modems, WiFi®, Bluetooth®, GPS, or any other wireless form of communication that is known.

The processing circuit 426 includes a Universal Serial Bus (USB) controller 425 which may be managed by the MPU 400.

The processing circuit 426 further includes a display controller 408, such as a NVIDIA® GeForce® GTX or Quadro® graphics adaptor from NVIDIA Corporation of America for interfacing with display 410. An I/O interface 412 interfaces with buttons 414, such as for volume control. In addition to the I/O interface 412 and the display 410, the processing circuit 426 may further include a microphone 441 and one or more cameras 431. The microphone 441 may have associated circuitry 440 for processing the sound into digital signals. Similarly, the camera 431 may include a camera controller 430 for controlling image capture operation of the camera 431. In an exemplary aspect, the camera 431 may include a Charge Coupled Device (CCD). The processing circuit 426 may include an audio circuit 442 for generating sound output signals, and may include an optional sound output port.

The power management and touch screen controller 420 manages power used by the processing circuit 426 and touch control. The communication bus 422, which may be an Industry Standard Architecture (ISA), Extended Industry Standard Architecture (EISA), Video Electronics Standards Association (VESA), Peripheral Component Interface (PCI), or similar, for interconnecting all of the components of the processing circuit 426. A description of the general features and functionality of the display 410, buttons 414, as well as the display controller 408, power management controller 420, network controller 406, and I/O interface 412 is omitted herein for brevity as these features are known.

Database

The neuroQWERTY MIT-CSXPD database, which is publicly available from the PhysioNet (research resource for complex physiologic complex signals), may be used to demonstrate an exemplary implementation for early detection of PD. It should be understood that a practical implementation would use a larger data set of patient data. The exemplary data contains keystroke logs collected from 85 subjects with and without PD. This dataset was collected and analyzed for investigating if the routine interaction with computer keyboards can be used to detect motor signs in the early stages of the PD subjects whose average time since diagnosis was 3.9 years, who were on PD medication but had no medication for the 18 hours before the typing test. See L. Giancardo, A. Sanchez-Fe rro, T. Arroyo-Gallego, I. Butterworth, C. S. Mendoza, P. Montero, M. Matarazzo, J. A. Obeso, M. L. Gray, and R. San Jose Estepar, "Computer keyboard interaction as an indicator of early Parkinson's disease," Sci. Rep., vol. 6, pp. 34468, October 2016, which is incorporated herein by reference in its entirety. The subjects were recruited from two movement disorder units in Madrid, Spain, following the institutional protocols approved by the Massachusetts Institute of Technology, USA, Hospital 12 de Octubre, Spain, and Hospital Clinico San Carlos, Spain.

Each data file collected includes the timing information collected during the sessions of typing activity using a standard word processor on a Lenovo G50-70 i3-4005U with 4 MB of memory and a 15 inches screen running Manjaro Linux. The lengths of computer-key hold time series are highly variable, some have around 500, and others around 2500 time points.

Subjects were instructed to type as they normally would do at home and they were left free to correct typing mistakes only if they wanted to. The key acquisition software presented a temporal resolution of 3/0.28 (mean/standard deviation) milliseconds. Along with the raw typing collections, clinical evaluations were also performed on each subject, including UPDRS-III (Unified Parkinson's Disease Rating Scale: Part III) and finger tapping tests. See P. Martinez-Martin, A. Gil-Nagel, L. M. Gracia, and J. B. Gomez, J. Martinez-Sarries, F. Bermejo, and The Cooperative Multicentric Group, "Unified Parkinson's disease rating scale characteristics and structure," Mov. Disord., vol. 9, no. I, pp. 76-83, January 1994, which is incorporated herein by reference in its entirety.

Results and Discussion

Outliers may exist in the raw time series of the healthy control (HC) and PD individuals, where several data points are in the magnitude of $10^9$, were removed from the time series. See T. D. Pham, "Pattern analysis of computer keystroke time series in healthy control and early-stage Parkinson's disease subjects using fuzzy recurrence and scalable recurrence network features," J Neurosci. Methods, vol. 307, pp. 194-202, September 2018, which is incorporated herein by reference in its entirety. In order to classify the signals of short lengths, short segments from the start of the original time series may be selected for testing the use of the LSTM neural-network model with FRPs.

FIGS. 5A, 5B, 5C, 5D show two short time series of 30 time steps of the computer-key hold durations, extracted from the start of the original time series, recorded from a healthy control (HC) and early PD subjects, and their associated FRPs with an embedding dimension=1, time delay=1, and number of clusters=6 for FRPs. It can be observed from FIG. 5 that the FRPs display rich information as texture images as the values of the fuzzy membership grades about the recurrences of the underlying dynamics of the time series of the two subjects. Therefore, the fuzzy membership grades of the phase-space vectors of the time series were used as the feature with dimensions being equal to the number of the phase-space vectors for training and classification using the LSTM network.

The LSTM neural network of the MATLAB deep learning toolbox (R2018b) is used as the example implementation. The number of hidden layers=100, maximum number of epochs=200, and learning rate=0.001. $L_2$ regularization was used for the biases, input weights, and recurrent weights to reduce model overfitting. To construct FRPs, FCM parameters that are the fuzzy weighting exponent w, the number of clusters c, and the maximum number of iterations were chosen to be 2, 6, and 100, respectively. Given an embedding dimension m, time delay $\tau$, the number of the phase-space vectors of a time series of length L, which is also the number of feature dimensions used in the LSTM network, is calculated as $N=L-(m-1)\tau$. Thus, keeping $\tau=1$, the feature dimensions for m=1, 3, and 5 for L=50 are 50, 48, and 46, respectively; and for L=30, the feature dimensions for m=1, 3, and 5 are 30, 28, and 26, respectively. The time delay was set to be 1 for both lengths of the time series. There are methods for estimating the time delay and embedding dimension for the phase-space reconstruction such as the false nearest neighbor (FNN) and average mutual information (AMI), respectively, where the first local minima of the FNN and AMI functions are indicative of the embedding dimension and time delay, respectively. However, estimate for the embedding dimension and time delay for the phase-space reconstruction of each time series of the computer-key hold duration is not convenient for implementing the LSTM network because of the variation in the feature dimensions. It has been reported that the use of time delay=1 is well adopted for studying nonlinear time series, and several embedding dimensions were adopted in this study. See H. Kantz and T. Schreiber, Nonlinear Time Series Analysis. 2nd ed. Cambridge: Cambridge University Press, 2004.

Cross validation may be performed with two separate data sets, one data set is used for training and the other data set is used for testing, then training and testing are repeated by swapping the two data sets.

Tables II and III show the results of classifying HC and early PD subjects using the short time series of lengths 50 and 30, respectively. Values of the accuracy, sensitivity, and specificity are based on the average of five repetitions of the 10-fold cross validation results. The sensitivity, which is also called the true positive rate, measures the proportion of actual positives (early PD subjects) that are correctly identified as such; whereas specificity, which is also known as the true negative rate, measures the proportion of actual negatives (control subjects) that are correctly identified as such. The sensitivity (SEN) and specificity (SPE) are computed as follows.

$$SEN = \frac{TP}{TP + FN} \quad (13)$$

where TP and FN are the numbers of true positives and false negatives, respectively, which are obtained from the (2×2) confusion matrix for each classification method.

$$SPE = \frac{TN}{TN + FP} \quad (14)$$

where TN and FP are the numbers of true negatives and false positives, respectively, which are obtained from the (2×2) confusion matrix for each classification method.

For the direct use of the time series (LSTM-time series) of length=50, accuracy=63%, sensitivity=100%, and specificity=0%. For the use of FRPs of the time series (LSTM-FRP) of length=50, with embedding dimension m=1, accuracy=72%, sensitivity=90%, and specificity=47%; with m=3, accuracy=65%, sensitivity=67%, and specificity=63%; and for m=5, accuracy=63%, sensitivity=100%, and specificity=0%. The accuracy results obtained from the use FRPs are equal to or higher than the accuracy obtained from the direct use of the time series. With the use of FRPs as features, the accuracy decreases with increasing value for m, where the best accuracy is obtained with m=1. The direct use of the time series gives 100% for sensitivity but 0% for sensitivity, such results are not practically helpful because all are identified as early PD, which may lead to a large false positive rate.

In the present disclosure, by using texture features instead of grayscale values of the fuzzy recurrent plot (FRP) as multi-dimensional data for training and classification of short time series using an LSTM network, the LSTM will achieve greater classification performance by incorporating more effective features. In addition, such a texture-features-based LSTM will be more robust in handling various types of short time series because it is able to take into account local spatio-temporal properties of complex data, and it enables a significant reduction in training time and memory required by deep neural networks because the number of texture features can be much smaller than the size of the FRPs.

TABLE I

AVERAGE ACCURACY (%), SENSITIVITY (%), AND SPECIFICITY (%) RATE OBTAINED FROM CLASSIFICATION OF CONTROL AND EARLY PD USING SHORT TIME SERIES OF LENGTH = 50 AND DIFFERENT METHODS

| Method | Accuracy | Sensitivity | Specificity |
|---|---|---|---|
| ID-CNN | 64.71 ± 21.81 | 70.83 ± 24.92 | 58.33 ± 30.68 |
| LSTM-Time series | 63.43 ± 4.55 | 100 ± 0.00 | 0.00 ± 0.00 |
| CNN-GoogLeNet | 54.29 ± 18.63 | 65.00 ± 28.50 | 40.00 ± 27.89 |
| CNN-AlexNet | 37.14 ± 7.82 | 35.00 ± 28.50 | 40.00 ± 43.46 |
| LSTM-FRP (m = 1) | 72.00 ± 15.92 | 90.00 ± 22.36 | 46.67 ± 50.55 |
| LSTM-FRP (m = 3) | 65.14 ± 11.50 | 66.67 ± 33.33 | 63.33 ± 41.50 |
| LSTM-FRP (m = 5) | 63.43 ± 4.55 | 100 ± 0.00 | 0.00 ± 0.00 |

TABLE II

AVERAGE ACCURACY (%), SENSITIVITY (%), AND SPECIFICITY (%) RATE OBTAINED FROM CLASSIFICATION OF CONTROL AND EARLY PD USING SHORT TIME SERIES OF LENGTH = 30 AND DIFFERENT METHODS

| Method | Accuracy | Sensitivity | Specificity |
|---|---|---|---|
| ID-CNN | 64.71 ± 15.56 | 59.17 ± 32.26 | 66.67 ± 20.79 |
| LSTM-Time series | 62.10 ± 4.33 | 93.33 ± 14.91 | 10.00 ± 22.36 |
| CNN-GoogLeNet | 65.71 ± 21.67 | 70.00 ± 20.92 | 60.00 ± 27.89 |
| CNN-AlexNet | 68.57 ± 6.39 | 55.00 ± 11.18 | 86.67 ± 29.81 |
| LSTM-FRP (m = 1) | 72.38 ± 11.24 | 78.33 ± 21.73 | 66.67 ± 23.57 |
| LSTM-FRP (m = 3) | 81.90 ± 11.74 | 95.00 ± 11.18 | 66.67 ± 23.57 |
| LSTM-FRP (m = 5) | 70.10 ± 9.63 | 95.00 ± 11.18 | 36.67 ± 24.72 |

For the time series of shorter length=30, the direct use of the time series for LSTM network training and validation results in accuracy=62%, sensitivity=93%, and specificity=10%. Once again, while the sensitivity is very high, the specificity is very low. The results obtained from the direct use of the time series for both time-series of lengths=50 and 30 are similar in accuracy, sensitivity, and specificity. For the use of FRPs of the time series of length=30, with m=1, accuracy=72%, sensitivity=78%, and specificity=67%; with m=3, accuracy=82%, sensitivity=95%, and specificity=67%; and for m=5, accuracy=70%, sensitivity=95%, and specificity=37%. The FRPs with m=3 give the highest accuracy (82%) among the others. All accuracy results obtained from the FRPs are higher than those obtained from the direct use of the time series.

The standard deviations of the results obtained from the use of FRPs for signal length=50 with m=1 and 3 are higher than those of the raw time series, because some rates of accuracy obtained from the FRPs reached 100% and 85%, respectively. However, even the average accuracy obtained from the use of the raw signals of the same length is lower than those obtained from the FRPs, the average specificity (true negative rate that is the ability to correctly identify those without PD) obtained from using the raw signals is zero, which is obviously not useful at all (Table II). Similarly, the standard deviations of the accuracy results obtained from the use of FRPs for signal length=50 with m=1, 3, and 5 are higher than those of the raw time series, because some rates of accuracy obtained from the FRPs reached 83%, 100%, and 86%, respectively. Once again, even the average accuracy obtained from the use of the raw signals of the same length is lower than those obtained from the FRPs, the average specificity obtained from using the raw signals is very low (10%), which is not useful for the classification (Table III).

Figure 6A:
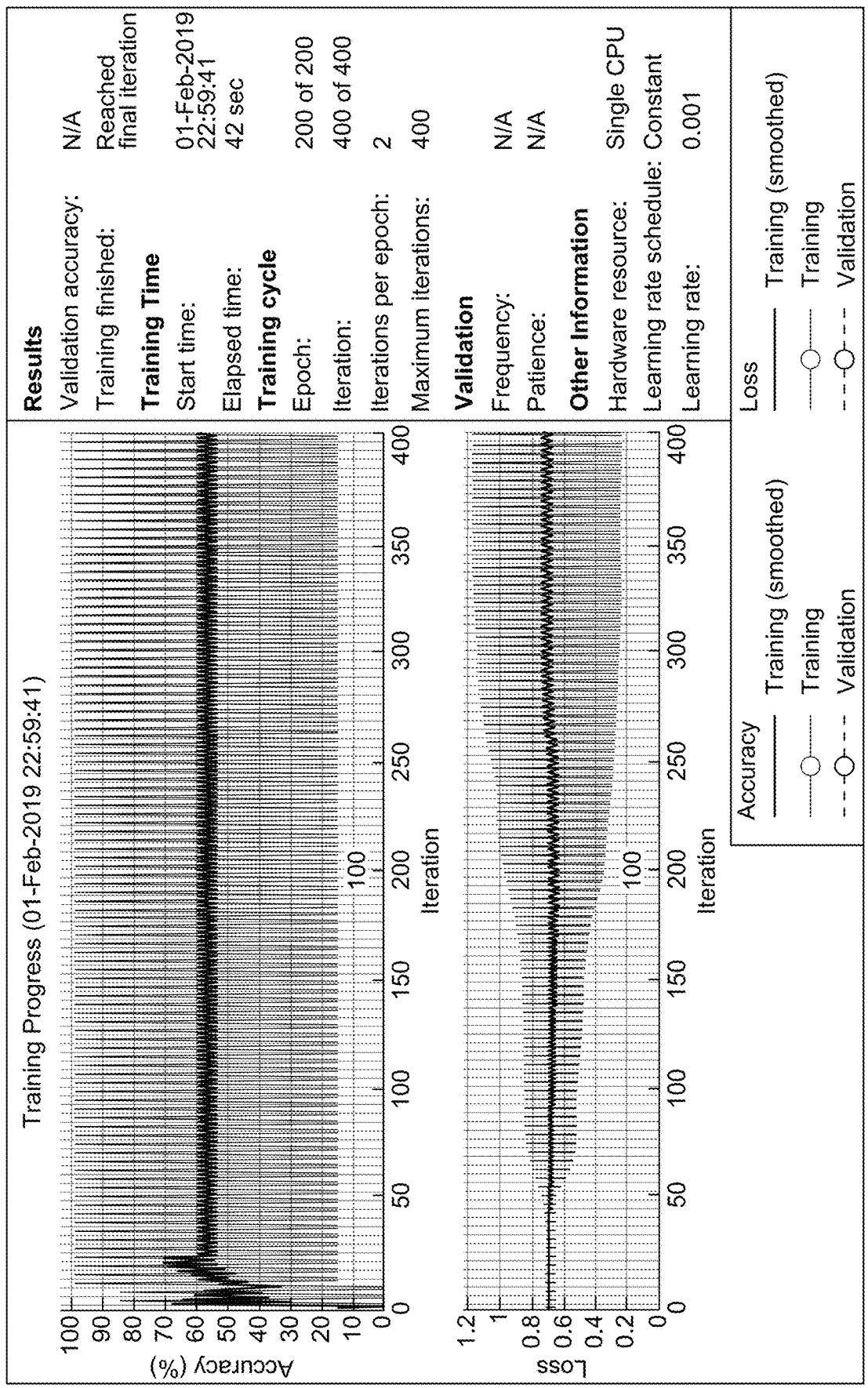
FIGS. 6A, 6B are graphs of training progress of LSTM neural network with short-key hold time series and FRPs with short-key hold time series.
Figure 6B:
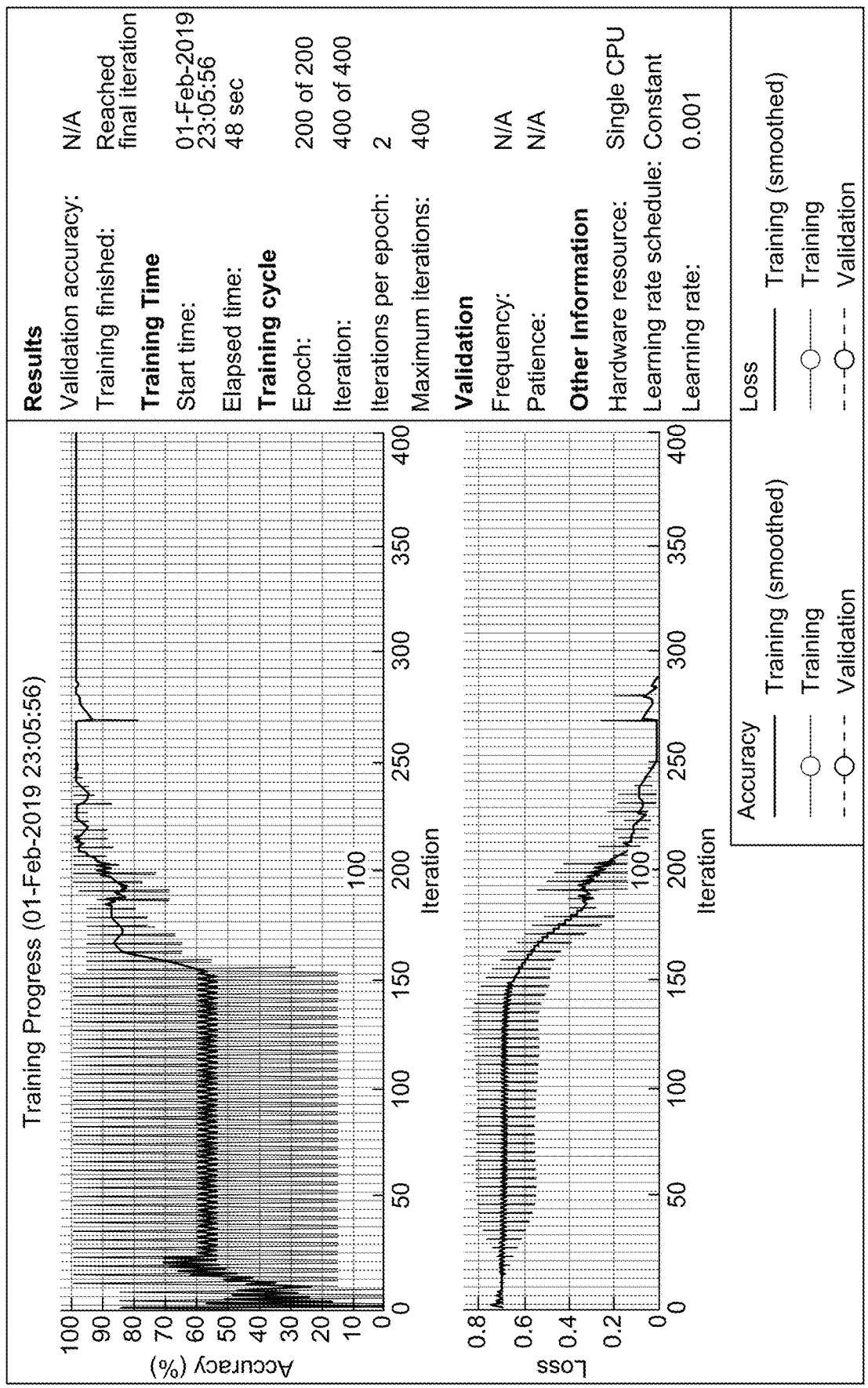

As an illustration for the performance of the FRPs preferred to that of the direct use of the short time series, FIGS. 6A and 6B show the training progresses and metrics of the LSTM network with the time series of length=30 and with the associated FRPs, respectively. Each iteration is an estimation of the gradient and an update of the network parameters. The accuracy of the direct use of the short time series converged to around 60% and the loss around 0.7, while the accuracy and loss for the use with the FRPs converged to 100% and 0, respectively. Furthermore, it can be observed that for the direct use of the time series in the LSTM network, the longer time series (L=50) yields higher accuracy than the shorter ones (L=30), but for the use with the FRPs, the accuracy depends on the selection of the embedding dimension (m) parameter, suggesting the influence of the embedding dimension over the time-series length. The accuracy values obtained from the direct input of the time series of two different lengths are similar, while these are highly variable for the FRPs. The augmentation of more training data for the two classes would be expected to reduce the accuracy variation obtained from the input of the FRPs. Another potential factor for the higher accuracy obtained from the FRPs of the shorter time series is the redundancy with respect to the higher feature dimensions provided by the FRPs of the longer time series. This factor also suggests the ability of FRPs to extract effective dynamical features from short time series with an appropriate selection of collective parameters for the phase-space reconstruction of different time series.

Tables II and III also show the average cross-validation results of classifying HC and early PD subjects obtained from two popular pre-trained deep CNNs known as GoogLeNet and AlexNet, using the short time series of lengths 50 and 30, respectively. See C. Szegedy, W. Liu, Y. Q. Jia, P. Sermanet, S. Reed, D. Anguelov, D. Erhan, V. Vanhoucke, and A. Rabinovich, "Going deeper with convolutions," in Proc. 2015 IEEE Conj. Computer Vision and Pattern Recognition, Boston, Mass., USA, 2015, pp. 1-9; A. Krizhevsky, I. Sutskever, and G. E. Hinton, "ImageNet classification with deep convolutional neural networks," Commun. ACM, vol. 60, no. 6, pp. 84-90, June 2017, each of which are incorporated herein by reference in their entirety. The implementations of these two pre-trained CNN models for time-series classification were based on the work proposed in MathWork, "Classify time series using wavelet analysis and deep learning," [Online]. Available: mathworks.com/help/deeplearning/examples/classify-time-series-using-wavelet-analysis-and-deep-learning.html. Accessed on: Apr. 25, 2019, which is incorporated herein by reference in its entirety. It is known that training a deep CNN from scratch is computationally expensive and requires a large amount of training data. In this implementation, a large amount of training data is not available. Thus, taking advantage of existing deep CNNs that have been trained on large data sets for conceptually similar tasks is desirable. This leveraging of existing neural networks is called transfer learning, which has recently been applied to time-series classification. See S. Karimi-Bidhendi, F. Munshi, and A. Munshi, "Scalable classification of univariate and multivariate time series," in Proc. IEEE Int. Conj. Big Data, Seattle, Wash., USA, 2019, pp. 1598-1605; H. I. Fawaz, G. Forestier, J. Weber, L. Idoumghar, and P. A. Muller, "Transfer learning for time series classification," in Proc. IEEE Int. Conf Big Data, Seattle, Wash., USA, 2018, pp. 1367-1376, each of which are incorporated herein by reference in their entirety. GoogLeNet and AlexNet, which were pretrained for image recognition, were adopted to classify transformed images of the short time series based on a time-frequency representation. Scalograms were used to obtain the RGB images of time-frequency representations of the time series. A scalogram is the absolute value of the continuous wavelet transform (CWT) coefficients of a signal. Parameters used for obtaining the scalograms of the time series and modifying GoogLeNet and AlexNet for the time-series classification are the same as described in Fawaz et al., 2018. For the time series of length=50, classification results obtained from both deep convolutional networks GoogLeNet (CNN-GoogLeNet) and AlexNet (CNN-AlexNet) are lower that LSTM-Time series and LSTM-FRP. CNN-AlexNet has the lowest average accuracy (37%). For the time series of shorter length=30, classification results obtained from CNN-AlexNet (69%) is higher than those obtained from the CNN-GoogLeNet and LSTM-Time series, but lower than the LSTM-FRP.

Figure 7A:
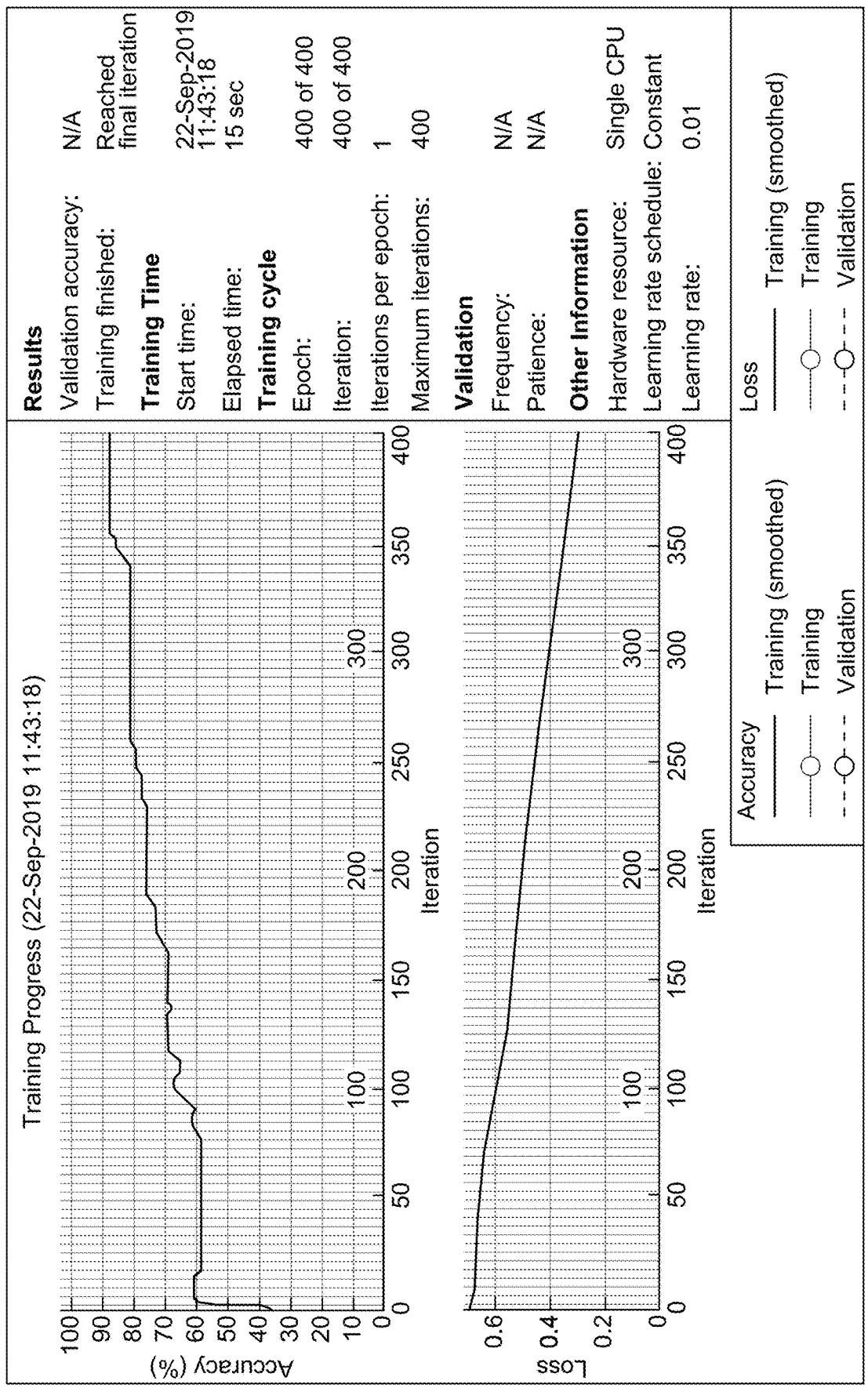
FIGS. 7A, 7B are graphs of training of computer-key hold time series with ID-CNN time-series length of 30 and time-series length of 50.
Figure 7B:
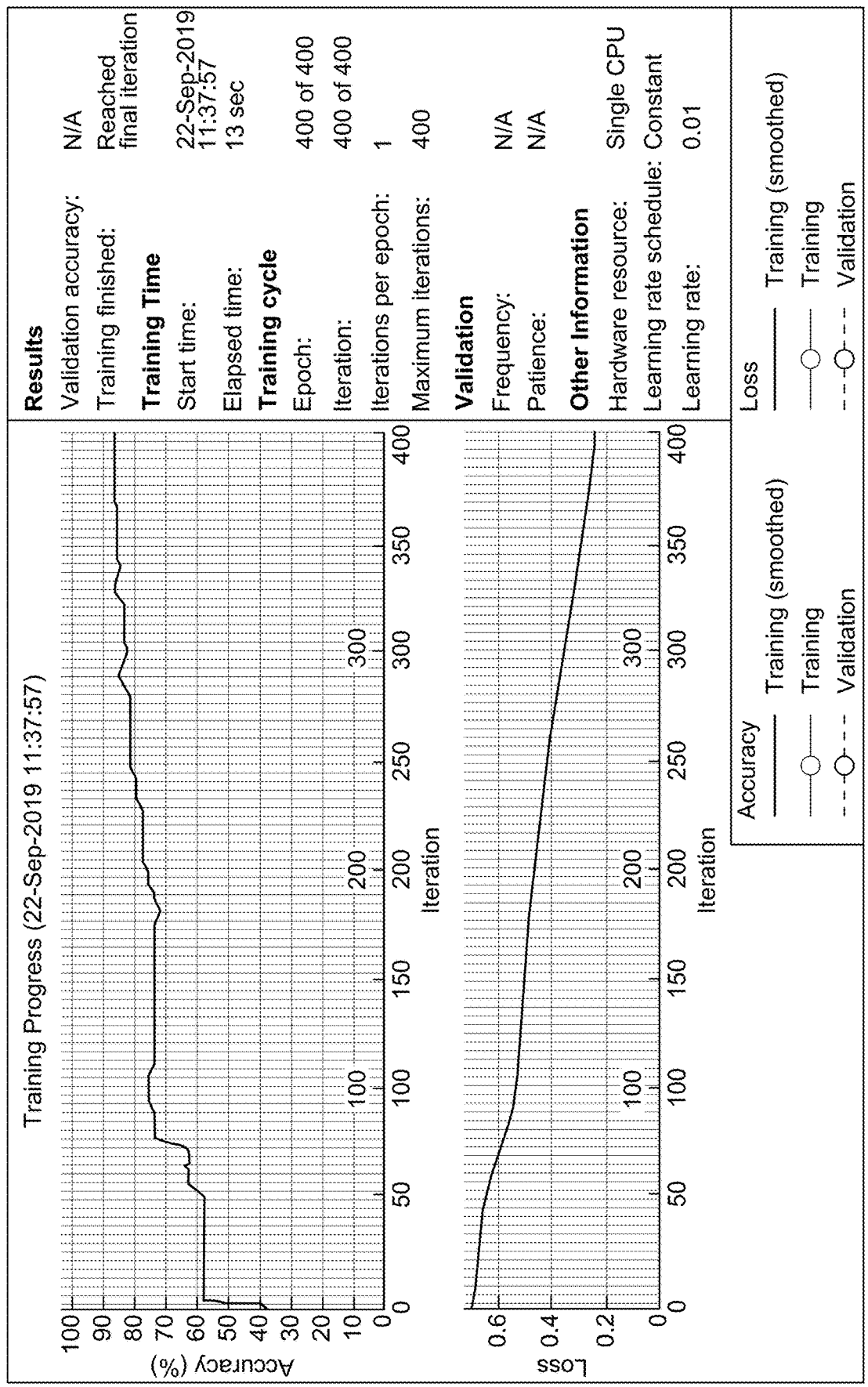

One-dimensional CNN (1D-CNN) was also applied as a baseline model for directly training and classifying the short time series. The CNN architecture of the MATLAB deep learning toolbox (2019a) was created as follows. The input size of the time series to the CNN model was specified as $L \times 1 \times 1$, where L is the length of the time series. A convolutional layer was constructed with 16 filters that have the height and width of 3. Padding was applied to the input along the edges. Padding was set so that the output size was the same as the input size where the stride is 1. A fully connected layer with an output size of 384 in the hidden layer and 2 as the output classes were specified. The maximum number of epochs was 400 for training the 1D-CNN. The average cross-validation results of classifying HC and early PD subjects using the time series of lengths=50, and 30 obtained from the 1D-CNN are shown in Tables II and III, respectively. For both time series of lengths=50 and 30, the 1D-CNN model provides similar classification accuracy rates in comparison with the LSTM directly using the time series (LSTM-Time series). However, the sensitivity and specificity obtained from the 1D-CNN are more balanced than those obtained from the LSTM-Time series. For time series length=50, LSTM-FRP models with m=1 and 3 outperform the 1DCNN, while the accuracy obtained from LSTM-FRP with m=5 is slightly slower than the 1D-CNN. For time series length=50, all LSTM-FRP models (m=1, 3, and 5) provide much higher classification accuracy rates than the 1D-CNN. FIGS. 7A and 7B show the training processes of the 1D-CNN with the time series of lengths=30 and 50. The converged accuracy and loss rates obtained from the 1D-CNN are less desirable than those from the LSTM-FRP (FIG. 6(B)).

In disclosed embodiments FRPs of short raw time series are used for classification with an LSTM network. In a comparison between the LSTM-based classification using raw time series and FRPs of raw time series, the FRP is constructed in order to correctly reflect the dynamics underlying the signal is mainly subject to the selection of a good embedding dimension m, whereas m being not applicable for the case of LSTM-based classification of raw time series. Hence, three different values of m were chosen for the construction of FRPs of the raw signals to gain insight into the influence of the embedding dimension over the classification. The LSTM-based classification using any of the three values form (except with m=5 for length=50, the accuracy rates of LSTM-FRP and LSTM-Time series are the same) specified for constructing the FRPs outperformed those using LSTM with raw time series and the two pre-trained CNN models.

Numerous modifications and variations of the present invention are possible in light of the above teachings. It is therefore to be understood that within the scope of the appended claims, the invention may be practiced otherwise than as specifically described herein.

The invention claimed is:

1. A method of classification of short time series in order to detect a neurodegenerative disorder, comprising:
receiving, by circuitry, a plurality of sensor data collected from subjects with and without the neurodegenerative disorder over a period of a few seconds as the short time series;
generating, by the circuitry, phase-space vectors from the plurality of sensor data in which each vector is a state of a dynamical system in space and time;

transforming, by the circuitry, the phase-space vectors into a grayscale image representing recurrences of a state-space vector in the same area of the phase space, wherein an intensity distribution of the grayscale image takes values in the range of 0 to 1;

for every pixel of the grayscale image, selecting, by the circuitry, a local window, where the respective pixel is at a center of the local window;

extracting, by the circuitry, temporal texture features of each window to obtain a multi-dimensional time series of D texture dimensions;

inputting, by the circuitry, the multidimensional time series, without the grayscale image, to a Long Short Term Memory (LSTM) network;

training the LSTM network by performing
  in an LSTM layer, inputting to a first LSTM block a first time step of the time series of D texture dimensions and determining a first output and an updated cell state,
  inputting to a next LSTM block a next time step of the time series of D texture dimensions, a current output and a current cell state and determining a next output and a next updated cell state, and
  continuing the inputting and the determining to LSTM blocks for each time step of the time series of D texture dimensions to output a final cell state; and classifying, by the LSTM network, the plurality of the sensor data as the neurodegenerative disorder or not.

2. The method of claim 1, wherein the extracted temporal texture features include a gray-level co-occurrence matrix (GLCM), local binary patterns (LBP), spatial statistics, and other texture properties, of each window.

3. The method of claim 1, further comprising:
  dividing, by the circuitry, the grayscale texture image into subimages having a width w<N pixels, where N is the width of the grayscale texture image in pixels.

4. The method of claim 3, wherein the subimages are a timewise extraction of the temporal texture features.

5. The method of claim 1, wherein the transformed values of the intensity distribution of the grayscale image in the range of 0 to 1 is a fuzzy membership function.

6. The method of claim 5, wherein the fuzzy membership function is a degree of relation of each pair of phase-space vectors and fuzzy clusters of the phase-space vectors.

7. The method of claim 6, wherein the transforming the phase-space vectors into the grayscale texture image includes computing, by the circuitry, the fuzzy membership function using a fuzzy c-means algorithm.

8. The method of claim 1, wherein the neurodegenerative disorder is Parkinson's disease (PD), and
  wherein the sensor data is of keystrokes collected from subjects with and without PD and is a time series in a range of 30 to 50 time steps of the keystroke hold duration.

9. A non-transitory computer-readable storage medium storing computer program instructions, which when executed by a computer perform a method of classification of short time series in order to detect a neurodegenerative disorder, comprising:
  receiving a plurality of sensor data collected from subjects with and without the neurodegenerative disorder over a period of a few seconds as the short time series;
  generating phase-space vectors from the plurality of sensor data in which each vector is a state of a dynamical system in space and time;
  transforming the phase-space vectors into a grayscale image representing recurrences of a state-space vector in the same area of the phase space, wherein the intensity distribution of the grayscale image takes values in the range of 0 to 1;
  for every pixel of the grayscale image, selecting a local window, where the respective pixel is at a center of the local window;
  extracting temporal texture features of each window to obtain a multi-dimensional time series of D texture dimensions;
  inputting the multidimensional time series, without the grayscale image, to a Long Short Term Memory (LSTM) network;
  training the LSTM network by:
    in an LSTM layer, inputting to a first LSTM block a first time step of the time series of D texture dimensions and determining a first output and an updated cell state,
    inputting to a next LSTM block a next time step of the time series of D texture dimensions, a current output and a current cell state and determining a next output and a next updated cell state, and
    continuing the inputting and the determining to LSTM blocks for each time step of the time series of D texture dimensions to output a final cell state; and
  classifying, by the LSTM network, the plurality of the sensor data as the neurodegenerative disorder or not.

10. The storage medium of claim 9, wherein the extracted temporal texture features include a gray-level co-occurrence matrix (GLCM), local binary patterns (LBP), spatial statistics, and other texture properties, of each window.

11. The storage medium of claim 9, further comprising:
  dividing the grayscale texture image into subimages having a width w<N pixels, where N is the width of the grayscale texture image in pixels.

12. The storage medium of claim 11, wherein the subimages are a timewise extraction of the temporal texture features.

13. The storage medium of claim 9, wherein the transformed values of the intensity distribution of the grayscale image in the range of 0 to 1 is a fuzzy membership function.

14. The storage medium of claim 13, wherein the fuzzy membership function is a degree of relation of each pair of phase-space vectors and fuzzy clusters of the phase-space vectors.

15. The storage medium of claim 14, wherein the transforming the phase-space vectors into the grayscale texture image includes computing the fuzzy membership function using a fuzzy c-means algorithm.

16. The storage medium of claim 9, wherein the neurodegenerative disorder is Parkinson's disease (PD), and
  wherein the sensor data is of keystrokes collected from subjects with and without PD and is a time series in a range of 30 to 50 time steps of the keystroke hold duration.

17. A method of classification of short time series in order to detect a neurodegenerative disorder, comprising:
  receiving, by circuitry, a plurality of sensor data collected from subjects with and without the neurodegenerative disorder over a period of a few seconds as the short time series;
  generating, by the circuitry, phase-space vectors from the plurality of sensor data in which each vector is a state of a dynamical system in space and time;
  transforming, by the circuitry, the phase-space vectors into a grayscale image representing recurrences of a state-space vector in the same area of the phase space, wherein the intensity distribution of the grayscale image takes values in the range of 0 to 1;

inputting, by the circuitry, the grayscale image representation to a Long Short Term Memory (LSTM) network; and classifying, by the LSTM network, the plurality of the sensor data as the neurodegenerative disorder or not;

wherein the neurodegenerative disorder is Parkinson's disease (PD), and wherein the sensor data is of keystrokes collected from subjects with and without PD and is a time series in a range of 30 to 50 time steps of the keystroke hold duration.

* * * * *